US012727750B2

United States Patent
(12) United States Patent
Pang et al.

(10) Patent No.: US 12,727,750 B2
(45) Date of Patent: Sep. 8, 2026

(54) SYSTEMS AND METHODS FOR OPTICAL FILTER DETECTION AND IDENTIFICATION

(71) Applicant: Stryker Corporation, Kalamazoo, MI (US)

(72) Inventors: Chien Mien Pang, San Jose, CA (US); Levey Trac Tran, Denver, CO (US); Ajay Ramesh, Pleasanton, CA (US); Katherine Jiang Lu, Cupertino, CA (US)

(73) Assignee: Stryker Corporation, Portage, MI (US)

( * ) Notice: Subject to any disclaimer, the term of this patent is extended or adjusted under 35 U.S.C. 154(b) by 152 days.

(21) Appl. No.: 18/393,596

(22) Filed: Dec. 21, 2023

(65) Prior Publication Data

US 2024/0206718 A1 Jun. 27, 2024

Related U.S. Application Data

(60) Provisional application No. 63/476,938, filed on Dec. 22, 2022.

(51) Int. Cl.
*A61B 1/045* (2006.01)
*A61B 1/06* (2006.01)

(52) U.S. Cl.
CPC ............ *A61B 1/0638* (2013.01); *A61B 1/045* (2013.01); *A61B 1/0646* (2013.01); *A61B 1/0655* (2022.02)

(58) Field of Classification Search
CPC ............ A61B 1/00006; A61B 1/00057; A61B 1/00059; A61B 1/00186; A61B 1/045;
(Continued)

(56) References Cited

U.S. PATENT DOCUMENTS

2011/0149057 A1 6/2011 Beck et al.
2018/0133507 A1* 5/2018 Malchano ............. G16H 40/63
(Continued)

FOREIGN PATENT DOCUMENTS

JP H06304135 A 11/1994
JP 2003235786 A 8/2003
JP 3619801 B2 2/2005

OTHER PUBLICATIONS

International Preliminary Report on Patentability mailed Jul. 3, 2025, direct to International Patent Application No. PCT/US2023/085398; 6 pages.

(Continued)

*Primary Examiner* — George Manuel
(74) *Attorney, Agent, or Firm* — Morrison & Foerster LLP

(57) ABSTRACT

Systems and methods for identifying optical filters within a surgical imaging device are provided. A system comprises a set of one or more light sources and a set of one or more image sensors of the surgical imaging device. The set of one or more light sources emits a set of one or more emission light pulses. The set of one or more image sensors detects reflection light of the one or more light pulses. The system determines, based at least in part on the detected reflection light, an identity of an optical filter of the surgical imaging device, wherein the optical filter is disposed in an optical collection path of the surgical imaging device.

25 Claims, 5 Drawing Sheets
(2 of 5 Drawing Sheet(s) Filed in Color)

(58) Field of Classification Search
CPC ... A61B 1/0638; A61B 1/0646; A61B 1/0655; A61B 2090/309; A61B 90/361; G01M 11/0285; G02B 23/2484; G02B 26/007; G02B 5/20; H04N 17/002; H04N 23/56
See application file for complete search history.

(56) References Cited

U.S. PATENT DOCUMENTS

| | | | |
|---|---|---|---|
| 2019/0231178 | A1 | 8/2019 | Kikuchi |
| 2020/0405135 | A1 | 12/2020 | Kojima |

OTHER PUBLICATIONS

International Search Report and Written Opinion mailed Mar. 15, 2024, directed to International Patent Application No. PCT/US2023/085398; 9 pages.

* cited by examiner

SYSTEMS AND METHODS FOR OPTICAL FILTER DETECTION AND IDENTIFICATION

CROSS-REFERENCE TO RELATED APPLICATIONS

This application claims the benefit of U.S. Provisional Application No. 63/476,938, filed Dec. 22, 2022, the entire contents of which are hereby incorporated by reference herein.

FIELD

This relates generally to surgical imaging devices, and more specifically to systems and methods for automatically detecting and identifying optical rejection filters in medical imaging devices.

BACKGROUND

Modern medical imaging systems, such as endoscopy systems, support numerous imaging modes that utilize different excitation wavelengths, different image capture protocols, and/or different image-processing operations. In some systems, different imaging modes are supported by a common light source, common image sensor, and/or common processor-based components such as a camera control unit (CCU) and/or image processing unit. In systems supporting multiple imaging modes, a user may select between different available imaging modes depending on intended application and/or user preference.

SUMMARY

As described above, modern medical imaging systems may support numerous different imaging modes between which users may select. However, those different imaging modes may in some instances require insertion and/or removal of different optical filters. In some instances, if one or more required optical filters are not present in an optical path (e.g., an optical path of collection light) of a medical imaging system, the desired imaging mode may be unable to function correctly, for example because images having undesired wavelengths or other undesired optical properties may be collected. Thus, when using medical imaging systems that provide for various different imaging modes, users must manually ensure that the correct filters are inserted in the system.

According to known techniques for ensuring that the correct filters are provided within the imaging system, users are required to manually know and recall the required filters for a desired imaging mode, and are further required to manually check (e.g., by visual inspection of optical filters) that the required filters are provided. These processes are prone to user error, and in the best case are time consuming, laborious, and inefficient.

Accordingly, there is a need for improved systems and methods for ensuring that a medical imaging system is provided with the correct set of one or more optical filters for use in a desired imaging mode. Specifically, there is a need for systems and methods that alleviate the requirement that a user manually recall which filter or filters are required for use with a desired imaging mode, and that quickly and automatically determine whether the required filters are (or are not) provided within the imaging system, without requiring manual visual inspection by the user. Disclosed herein are systems and methods that may address one or more of the above-identified needs.

In some aspects, a medical imaging system (e.g., an endoscope system) includes one or more light sources, one or more image sensors, and one or more processors. The one or more processors, for example provided as part of a CCU and/or an image processing unit, may be configured to control the light source(s) and image sensor(s) to perform a filter-detection and filter-identification protocol to automatically determine which (if any) optical filters are installed into the system and to determine, based thereon, whether one or more imaging modes may be used by the system To perform filter-detection and filter-identification, the system may emit one or more emission light pulses, and may detect reflected light therefrom (for example, reflected from a white-balance card or similar surface), wherein the reflected light may include zero or more collection light pulses.

The system may determine which wavelengths of collection light pulses were detected, how many pulses, and/or a temporal spacing of pulses, and may determine based thereon which optical filters are installed into the system. For example, the system may determine a wavelength of detected light, and may determine based thereon that certain wavelengths of light were not blocked by an optical rejection filter, and that said optical filter is therefore not installed in the system; alternatively or additionally, the system may determine that a certain wavelength of light was not detected, and may determine based thereon that certain wavelengths of light were blocked by an optical rejection filter, and that said optical rejection filter is therefore installed in the system.

The system may then determine whether one or more imaging modes may be executed, based on the determination as to which filters are or are not installed in the system. For example, the system may consult a lookup table to determine whether each required filter for a desired imaging mode is installed in the system, and to confirm that no incompatible filters for the desired imaging mode are installed in the system. If criteria for setting the mode are met, then the system may set one or more system components to the desired mode such that imaging of a subject in accordance with the selected mode may be performed. (In some aspects, a user may indicate which imaging mode is desired, and the system may confirm that the system is properly configured for the mode. In some aspects, the system may automatically select one or more imaging modes based on which filters are installed in the system, and may display imaging mode options from which a user can choose or may automatically set the system to an automatically selected mode.)

In some aspects, a system for identifying optical filters within a surgical imaging device is provided, the system comprising: a set of one or more light sources; a set of one or more image sensors of the surgical imaging device; one or more processors; and memory storing instructions configured to be executed by the one or more processors to cause the system to: emit, by the set of one or more light sources, a set of one or more emission light pulses; detect, by the set of one or more image sensors, reflection light of the one or more light pulses; and determine, based at least in part on the detected reflection light, an identity of an optical filter of the surgical imaging device, wherein the optical filter is disposed in an optical collection path of the surgical imaging device.

Optionally, emitting the set of one or more emission light pulses comprises emitting a predetermined time-series of emission light pulses selected to differentiate between a predetermined set of optical filters, wherein one or more of the emission light pulses have different characteristic wavelengths from one another.

Optionally, detecting the reflection light comprises detecting a set of collection light pulses, wherein one or more of the collection light pulses have different characteristic wavelengths from one another.

Optionally, determining the identity of the optical filter based at least in part on the detected reflection light comprises determining whether the detected reflection light exceeds a threshold intensity in a predetermined wavelength range.

Optionally, determining the identity of the optical filter based at least in part on the detected reflection light comprises determining whether a first image sensor of the set of one or more image sensors is activated above a threshold intensity.

Optionally, determining the identity of the optical filter based at least in part on the detected reflection light comprises determining that the reflection light comprises a number of collection light pulses that is fewer than a number of emission light pulses emitted in the set of one or more emission light pulses.

Optionally, detecting the reflection light comprises detecting multiple collection light pulses; and determining the identity of the optical filter based at least in part on the detected reflection light comprises determining the identity of the optical filter based at least in part on relative intensities of the multiple collection light pulses.

Optionally, determining the identity of the optical filter comprises looking up the identity filter based on stored data indicating an association between a characteristic of the detected reflection light and the identity of the optical filter.

Optionally, determining the identity of the optical filter comprises: determining, based at least in part on the detected reflection light, one or more optical characteristics of the optical filter; and determining, based at least in part on the determined one or more optical characteristics, the identity of the optical filter.

Optionally, the instructions are configured to be executed by the one or more processors to cause the system to, after determining the identity of the optical filter, determine one or more additional optical characteristics of the optical filter, different from the one or more optical characteristics, based on the determined identity of the optical filter.

Optionally, the instructions are configured to be executed by the one or more processors to cause the system to, after determining the identity of the optical filter, capture, by the set of one or more image sensors, an image of a subject.

Optionally, the instructions are configured to be executed by the one or more processors to cause the system to: select an image capture mode based at least in part on the determined identity of the optical filter; set the set of one or more image sensors to the selected image capture mode; and capturing the image of the subject comprises capturing the image in accordance with the image capture mode.

Optionally, the instructions are configured to be executed by the one or more processors to cause the system to approve a selected image capture mode for the set of one or more image sensors based at least in part on the determined identity of the optical filter; and capturing the image of the subject comprises capturing the image in accordance with the selected image capture mode.

Optionally, the instructions are configured to be executed by the one or more processors to cause the system to, after determining the identity of the optical filter, illuminate, by the one or more light sources, a subject to be imaged by the system.

Optionally, the instructions are configured to be executed by the one or more processors to cause the system to: select an illumination mode based at least in part on the determined identity of the optical filter; and set the set of one or more light sources to the selected illumination mode; and illuminating the subject comprises illuminating the subject in accordance with the illumination mode.

Optionally, the instructions are configured to be executed by the one or more processors to cause the system to approve a selected illumination mode for the set of one or more light sources based at least in part on the determined identity of the optical filter; and illuminating the subject comprises illuminating the subject in accordance with the illumination mode.

Optionally, the instructions are configured to be executed by the one or more processors to cause the system to, after determining the identity of the optical filter, perform an image processing operation on an image captured through the optical filter.

Optionally, the instructions are configured to be executed by the one or more processors to cause the system to: select an image processing mode based at least in part on the determined identity of the optical filter; and set the set of system to the selected image processing mode; and performing the image processing operation comprises performing the image processing operation in accordance with the image processing mode.

Optionally, the instructions are configured to be executed by the one or more processors to cause the system to approve a selected image processing mode for the system based at least in part on the determined identity of the optical filter; and performing the image processing operation comprises performing the image processing operation in accordance with the image processing mode.

Optionally, the instructions are configured to be executed by the one or more processors to cause the system to: select a mode for the system based at least in part on the determined identity of the optical filter; and set the set of system to the selected mode.

Optionally, the instructions are configured to be executed by the one or more processors to cause the system to: approve a selected mode for the system based at least in part on the determined identity of the optical filter.

Optionally, the optical filter is disposed in a coupler of the system.

Optionally, the optical filter is disposed between the surgical imaging device and a coupler of the system.

Optionally, the surgical imaging device comprises an endoscope and the optical filter is disposed in the endoscope.

In some aspects, a non-transitory computer-readable storage medium storing instructions for identifying optical filters within a surgical imaging device is provided, the instructions configured to be executed by one or more processors of system comprising a set of one or more light sources and a set of one or more image sensors of the surgical imaging device, to cause the system to: emit, by the set of one or more light sources, a set of one or more emission light pulses; detect, by the set of one or more image sensors, reflection light of the one or more light pulses; and determine, based at least in part on the detected reflection light, an identity of an optical filter of the surgical imaging device, wherein the optical filter is disposed in an optical collection path of the surgical imaging device.

In some aspects, a computer program product comprises software code portions including instructions for identifying optical filters within a surgical imaging device is provided, the instructions configured to be executed by one or more processors of system comprising a set of one or more light sources and a set of one or more image sensors of the surgical imaging device, to cause the system to: emit, by the set of one or more light sources, a set of one or more emission light pulses; detect, by the set of one or more image sensors, reflection light of the one or more light pulses; and determine, based at least in part on the detected reflection light, an identity of an optical filter of the surgical imaging device, wherein the optical filter is disposed in an optical collection path of the surgical imaging device.

In some aspects, a method for identifying optical filters within a surgical imaging device is provided, the method performed by a system comprising a set of one or more light sources, a set of one or more image sensors of the surgical imaging device, and one or more processors, the method comprising: emitting, by the set of one or more light sources, a set of one or more emission light pulses; detecting, by the set of one or more image sensors, reflection light of the one or more light pulses; and determining, based at least in part on the detected reflection light, an identity of an optical filter of the surgical imaging device, wherein the optical filter is disposed in an optical collection path of the surgical imaging device.

It will be appreciated that any of the variations, aspects, features and options described in view of the systems apply equally to the methods and vice versa. It will also be clear that any one or more of the above variations, aspects, features and options can be combined.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention will now be described, by way of example only, with reference to the accompanying drawings, in which.

DETAILED DESCRIPTION

It will be appreciated that any of the variations, aspects, features and options described in view of the systems apply equally to the methods and vice versa. It will also be clear that any one or more of the above variations, aspects, features and options can be combined.

Exemplary System

Figure 1:
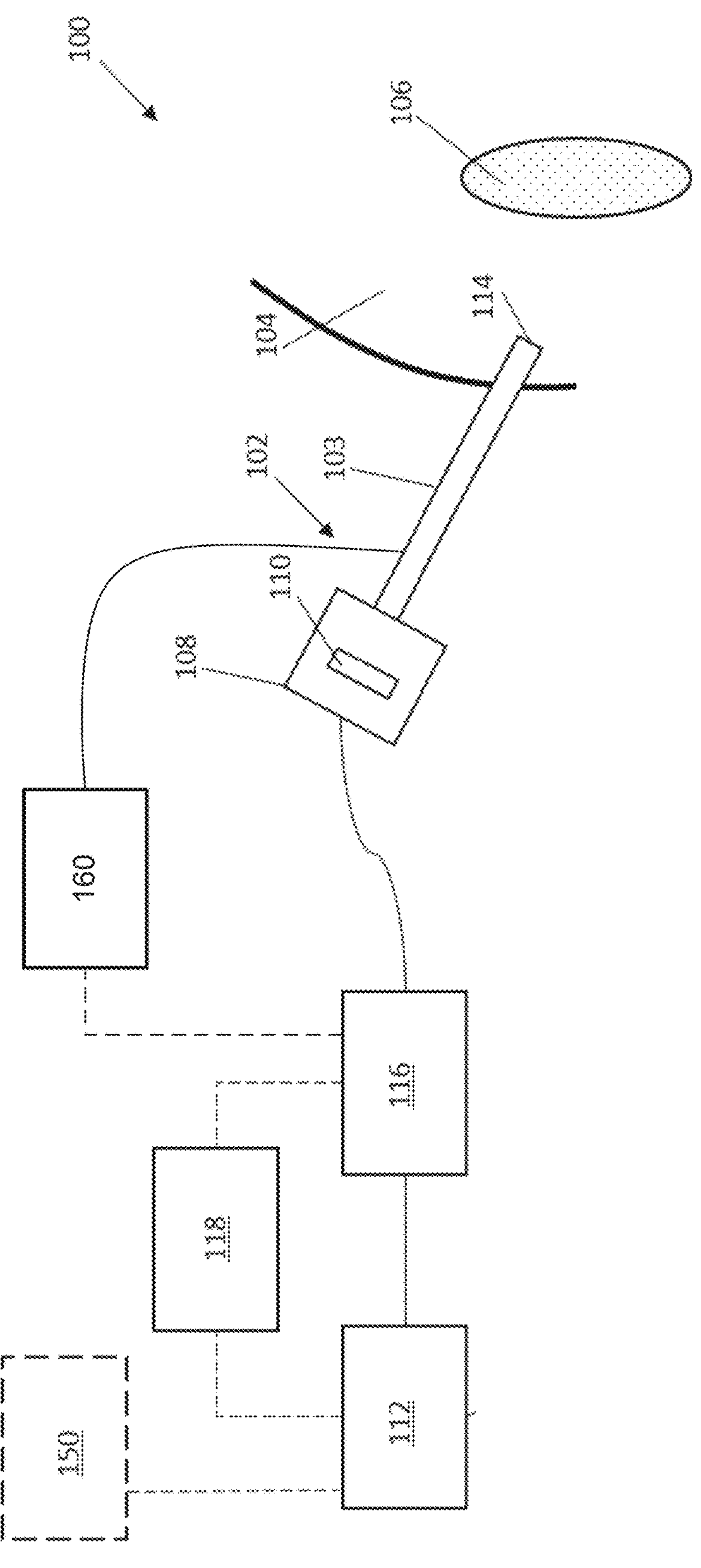
FIG. 1 shows a medical imaging system configured to automatically detect and identify one or more optical filters installed in the system, according to some aspects.

FIG. 1 illustrates an exemplary endoscopy system 100, according to examples of the disclosure. As described herein, system 100 may be configured for automatically detecting and identifying one or more optical filters.

System 100 includes an endoscopic imaging device 102 for insertion into a surgical cavity 104 for imaging tissue 106 within the surgical cavity 104 during a medical procedure. The endoscopic imaging device 102 may include an endoscope 103 that extends from an endoscopic camera head 108 that includes one or more imaging sensors 110. Light reflected and/or emitted (such as fluorescence light emitted by fluorescing targets that are excited by fluorescence excitation illumination light) from the tissue 106 is received by the distal end 114 of the endoscope 103. The light is propagated by the endoscope 103, such as via one or more optical components (for example, one or more lenses, prisms, light pipes, or other optical components), to the camera head 108, where it is directed onto the one or more imaging sensors 110. In one or more examples, one or more filters (not shown) may be included in the endoscope 103 and/or camera head 108 for filtering a portion of the light received from the tissue 106 (such as fluorescence excitation light). While the example above describes an example implementation of an endoscopic imaging device, the example should not be seen as limiting to the disclosure and the systems and methods described herein can be implemented using other imaging devices that are configured to image a patient during surgery.

The one or more imaging sensors 110 generate pixel data that can be transmitted to a camera control unit 116 that is communicatively connected to the camera head 108. The camera control unit 116 generates a video feed from the pixel data that shows the tissue being viewed by the endoscopic imaging device 102 at any given moment in time. In one or more examples, the video feed can be transmitted to an image processing unit 112 for further image processing, storage, display, and/or routing to one or more remote computing systems 150 such as a cloud computing system. The video feed or portions thereof can be transmitted to one or more displays 118, from the camera control unit 116 and/or the image processing unit 112, for visualization by medical personnel, such as by a surgeon for visualizing the surgical cavity 104 during a surgical procedure on a patient.

Imaging device 102 may include one or more light sources, each of which may include one or more lasers, diodes, LEDs, and/or any other suitable light source type. In the example of FIG. 1, system 100 includes light source 160, which is optically coupled to endoscopic imaging device 102 such that light from light source 160 is delivered (e.g., via a light cable or light cord) down endoscopic imaging device 102 such that the light from light source 160 may be emitted from the top of endoscopic imaging device 102. Optionally, system 100 may include a light source that is provided as a component of imaging device 102. Light source 160 may be controlled by camera control unit 116, which may synchronize functions of light source 160 with functions of other components of system 100, for example to execute the techniques described herein. Additionally or alternatively, light source 160 may be controlled by one or more processors disposed elsewhere in system 100.

Imaging device 102 may include one or more optical filters (not shown), for example optical rejection filters that reject certain wavelengths of light while allowing certain other wavelengths of light to transmit therethrough. The one or more filters may be disposed in an optical path of collection light of imaging device 102, for example by being disposed on or near distal end 114 of endoscope 103, in a shaft of endoscope 103, at a juncture between endoscope 103 and endoscopic camera head 108, between endoscope 103 and a coupler attached thereto, within the coupler, and/or within endoscopic camera head 108. Imaging device 102 may be configured such that one or more of the optical filters may be inserted (installed) into and removed (uninstalled) from imaging device 102. A user may manually insert and/or remove filters from an optical path for collection light, and/or filters may be inserted and/or removed from the optical path for collection light using one or more automated devices such as a filter wheel or translational stage.

Exemplary Method

Figure 2:
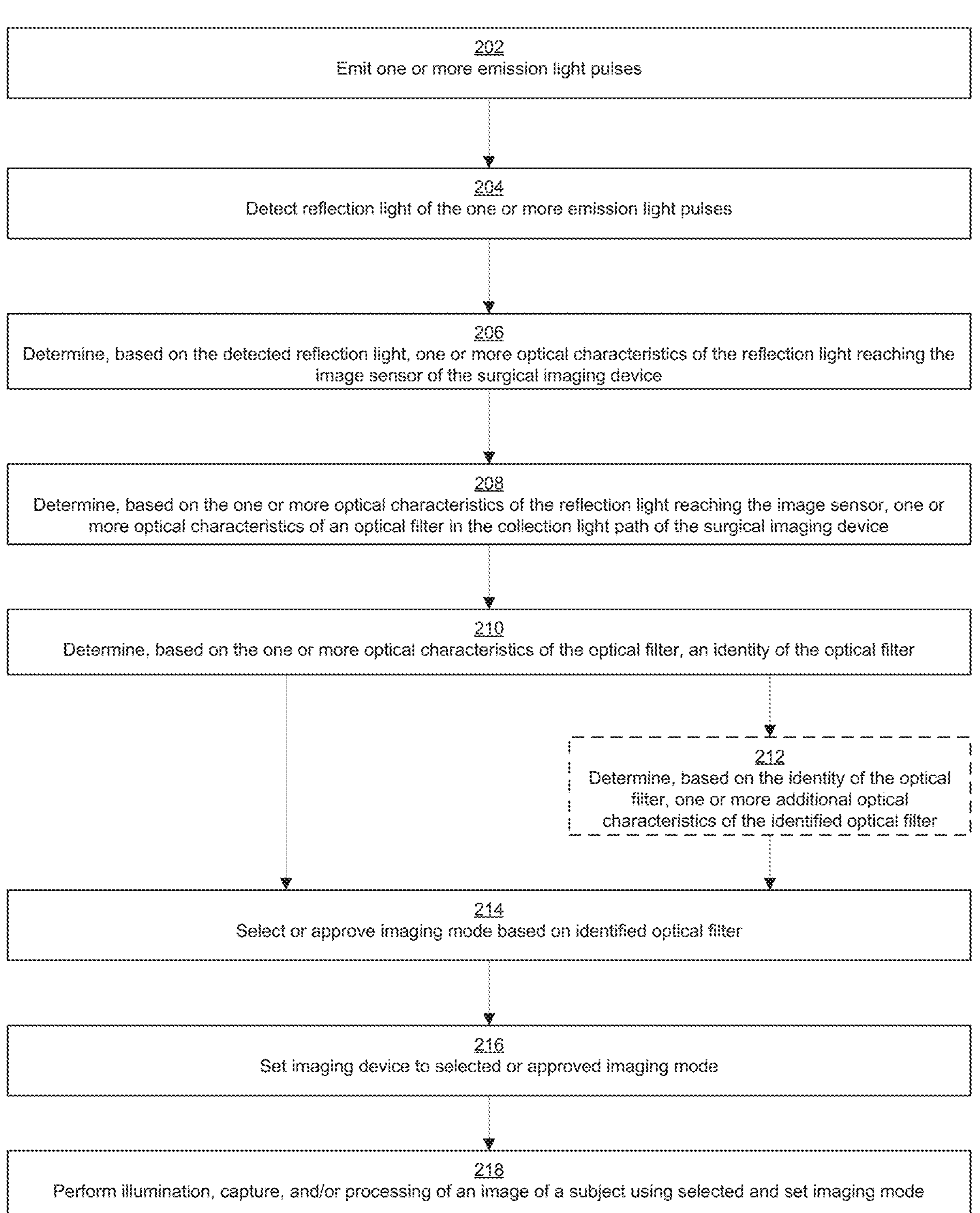
FIG. 2 depicts a method for automatically detecting and identifying one or more optical filters installed in a medical imaging system, according to some aspects.

FIG. 2 depicts a method 200 for automatically detecting and identifying one or more optical filters installed in a medical imaging system, according to some aspects. Method 200 may be performed by an imaging system, including any suitable medical imaging system, such as system 100 described above with respect to FIG. 1. As described below, method 200 may be performed by an endoscopic imaging system such as system 100, in which the system may cause one or more light sources of the system to emit emission light, one or more image sensors of the system to detect (filtered or unfiltered) reflection light from the emission light, and one or more processors of the system to determine, based on the detected reflection light, information regarding what optical filters are or are not installed in the system. In some aspects, method 200 may be performed in response to a user instructing the system to perform a filter detection process, in response to a user instructing the system to perform a white-balance process, and/or in response to any other suitable trigger condition. The method 200 may be performed prior to medical imaging of a subject being performed using the medical imaging system.

At block 202, the system may emit one or more emission light pulses. For example, system 100 may cause one or more light sources to emit emission light to illuminate and/or excite a target.

The one or more light sources may be mounted on an imaging device such as imaging device 102 and/or endoscope 103, and/or the one or more light sources may be provided separately from an imaging device of the system.

The one or more emission light pulses may be emitted as part of a predetermined filter testing protocol. For example, a user may aim the light source(s) (separately or together with the imaging device) at a reflective target such as a white balance card, and the user may execute a command (e.g., by pressing a button on a user input device, or by executing a voice command) to initiate a filter testing protocol. In response to the user command, the light source(s) may emit one or more light emission pulses as part of a predetermined filter testing protocol.

In some aspects, the filter testing protocol may be a universal filter testing protocol that is executed, regardless of one or more other system settings, to attempt to determine which (if any) optical filters are installed in the system.

In some aspects, the filter testing protocol may be a special-purpose filter testing protocol that is selected by the user from a set of options, or that is automatically selected by the system from a set of options. The system may automatically select a special-purpose filter testing protocol in accordance with a user's indication of a desired imaging mode, in accordance with one or more system settings, and/or in accordance with a user's selection of one or more medical or surgical procedures associated with a desired imaging mode. For example, the system may determine an imaging mode based on system settings and/or user inputs, may automatically determine what filters are required (and/or which are impermissible) for execution of the imaging mode, and may automatically select a special-purpose filter testing protocol that will test for the presence of the required filters (and/or for the absence of the impermissible filters).

In some aspects, the one or more emission light pulses may include a single pulse, a plurality of pulses emitted wholly or partially simultaneously with one another, and/or a plurality of pulses emitted in a time series with respect to one another. In some embodiments, different pulses in time series may be spaced apart from one another with regular and/or irregular spacing. In some embodiments, different pulses that are wholly or partially simultaneous with one another and/or that are in time series with one another may have the same or different temporal pulse lengths from one another.

In some aspects, the one or more emission light pulses may have one or more characteristic wavelengths. For example, different pulses having different characteristic wavelengths may be emitted simultaneously with one another, and/or different pulses having different characteristic wavelengths may be emitted one after another in time series.

In some aspects, the one or more emission light pulses may have one or more additional optical characteristics that may be the same or different across different pulses, wherein the optical characteristics may include, for example, spot size, beam shape, polarization, and/or intensity.

Optical characteristics (including wavelengths and other characteristics) as well as temporal information (e.g., pulse length, duty cycle, and/or other timing schema information) may be shared in memory by the system such that the system can cause the one or more light sources to emit the emission pulses in accordance with the selected filter testing protocol.

At block 204, the system may detect the presence and/or absence of reflection light of the one or more emission light pulses. In some implementations, the emission light pulses may be incident on a surface such as a white balance card or other test target used to perform the filter testing protocol, and light from the one or more emission light pulses may reflect off of the test target. As the reflected light travels back from the test target to one or more image sensors of the imaging system, the reflected light may pass through zero or more optical filters that are present in the optical collection path of the system. The zero or more optical filters may reject some amount of the reflected light. The optical filters may be wavelength-dependent, such that only certain wavelengths of reflected light are blocked while other wavelengths of reflected light are allowed to pass through to the one or more image sensors. The system may use the presence of one or more reflection light pulses and/or the absence of one or more reflection light pulses to determine what filters are or are not present, as described further hereinbelow.

In some aspects, one or more additional optical components, such as polarizers, beam-splitters, and the like, may be present in the optical collection path. Optionally, the system may be configured to determine the presence or absence of one or more other optical components, and/or to determine an identity of one or more other optical components, in a same or similar manner as described herein with respect to identifying optical filters.

While the exemplary disclosure herein primarily contemplates reflected light (reflected from light emitted from a light source) being detected as part of the filter testing protocol, in some aspects the system may be configured to (additionally or alternatively) detect fluorescence emission light that is emitted from an excited target in response to fluorescence excitation light emitted from a light source.

At block 206, the system may determine, based at least in part on the detected reflection light (and/or lack of detected reflection light), one or more optical characteristics of the detected reflection light reaching the image sensor of the imaging device.

The system may process signals generated by the one or more optical sensors to process the detected light. A single frame and/or multiple frames may be analyzed by the system. A single pixel, multiple different individual pixels, a single set of pixels, multiple different sets of pixels, and/or an entire frame may be analyzed by the system.

In some implementations, the system may determine one or more wavelength (e.g., color) characteristics of the detected reflection light. For example, the system may determine intensities in one or more different color channels for an analyzed area (e.g., a pixel, set of pixels, and/or frame). In some implementations, the system may determine an average intensity for a color channel for an analyzed region. In some implementations, the system may spectrally analyze detected light to determine one or more peak-intensity wavelengths of the detected reflection light.

In some implementations, the system may determine one or more intensity characteristics of the detected reflection light, for example by determining a maximum intensity, average intensity, and/or other intensity of one or more pulses across one or more frames for an analyzed region.

In some implementations, the system may determine one or more pulse characteristics of the detected reflection light, for example by resolving the detected reflection light into zero or more pulses to determine a number of collection light pulses detected by the system. Optionally, the system may determine timing information for one or more resolved collection light pulses, for example by determining whether the collection light pulses are wholly or partially simultaneous with one another and or a temporal spacing by which the collection light pulses are spaced from one another. Depending on the number and characteristics of optical filters present in the collection light path, one or more pulses of reflection light may be blocked from being transmitted to the image sensor(s) (or may be attenuated upon reaching the image sensor(s)), and the system may subsequently determine that a number of pulses of detected reflection light is fewer than a number of pulses of emission light.

At block 208, the system may determine, based at least in part on the one or more optical characteristics of the detected reflection light (or lack thereof) reaching the image sensor of the imaging device, one or more optical characteristics of one or more optical filters in the collection light path of the imaging device.

The system may determine, based on color characteristics of the detected reflection light, that optical filters having properties that block wavelengths of light that were collected are not present in the optical collection path. For example, if the system detects one or more pulses of blue light, the system may determine that blue-light-blocking filters are not present in the optical collection path.

The system may determine optical characteristics of filters in the optical collection path based on the color characteristics of the detected reflection light and further based on the color characteristics of the emission light emitted by the light source(s). For example, if blue light is emitted from the light source(s) and is expected to be reflected from a white balance card as blue reflection light, then the absence of blue light from the collected light may indicate the presence of a blue-light-blocking filter. On the other hand, if blue light is not emitted from the light source(s) and is therefore not expected to be reflected from a white balance card as blue reflection light, then the absence of blue light from the collected light may not indicate the presence (or absence) of a blue-light blocking filter. The system may access data indicating which colors of emission light were emitted in order to compare those colors to the colors of emission light that are detected. In this manner, if certain wavelengths that were included in the emission light are "missing" from the detected reflection light, then the system may determine that filters in the optical collection path have optical properties that block transmission of those certain wavelengths.

Optionally, the system may determine optical characteristics of filters in the optical collection path based on other characteristics of the detected light aside from (or in addition to) color characteristics.

For example, in an instance in which the system emits two pulses in series of blue light followed by only a single pulse of red light, and the system detects only a single pulse of detection light, the system may determine (even in the absence of determining color characteristics of the detected light) that reflections of the single red pulse were detected while reflections of the two blue pulses were blocked. Thus, the system may determine that filters in the optical collection path have blue-light blocking properties and do not have red-light blocking properties.

In another example, in an instance in which the system emits blue light pulses at a first timing pattern (e.g., a first temporal spacing) and detects red light pulses at a second timing pattern (e.g., a second temporal spacing), and the system detects reflected pulses following the first timing pattern (e.g., having the first temporal spacing), the system may determine (even in the absence of determining color characteristics of the detected light) that reflections of the blue light pulses were detected while reflections of the red light pulses were blocked. Thus, the system may determine that filters in the optical collection path have red-light blocking properties and do not have blue-light blocking properties.

In some aspects, the system may determine optical properties of one or more optical filters in the collection light path of the imaging device by quantifying optical properties of the collection light path, for example by assigning one or more numerical values to characterize wavelengths at which the filters block or transmit light, percentages of light at given wavelengths that are allowed to pass, or the like. In some aspects, the system may determine optical properties of one or more optical filters in the collection light path of the imaging device by selecting one or more optical property classifications from a predefined set of classifications, for example by assigning the optical path a "red light blocking" or "red light permitting" or "blue light blocking" label.

At block 210, the system may determine, based at least in part on the one or more determined optical characteristics of the one or more optical filters in the collection light path, one or more respective identities of the optical filters in the collection light path. The system may consult a lookup table or other stored data to match determined optical properties of the one or more optical filters to stored data representing the identities (e.g., filter labels) for one or more optical filters matching those optical properties. For example, if the system determines that the optical collection path includes a filter that blocks light at 700 nm, the system may lookup data in a lookup table that indicates an identity of (e.g., a label for) a filter that blocks light at 700 nm.

In some aspects, the system may generate output data indicating the determined filter identity, for example by causing an indication of the filter identity to be displayed or transmitted. In some aspects, if the system is unable to determine a filter identity, the system may generate and output an error indication. In some aspects, if the system identifies multiple candidate filters that may be present in the collection light path, the system may automatically perform additional filter testing (or instruct the user to perform additional filter testing) to further attempt to distinguish between multiple candidate filters.

At block 212, the system may determine, based at least in part on the determined identities of the one or more optical filter, one or more additional respective optical characteristics of the one or more identified optical filter. The system may consult a lookup table or other stored data to match determined filter identities (e.g., filter labels) to stored data representing respective additional optical properties for the one or more identified optical filters. For example, if the system determined an identity of an optical filter based at least in part on its color-filtering properties, the system may look up data indicating a polarization, overall transmissivity, radius of curvature, and/or other optical property (different from the previously-determined color filtering property) of the filter.

At block 214, the system may select or approve an imaging mode based at least in part on the identified optical filter. After determining an identity of an optical filter in the collection light path of the system, the system may determine whether the system is configured with all required filters installed (and with no impermissible filters installed) for operation in one or more imaging modes.

Optionally, a user may indicate a desired imaging mode, and the system may automatically determine whether all required filters (and no impermissible filters) are installed for operation in the desired imaging mode. Optionally, the system may automatically determine a desired imaging mode based on one or more algorithms (e.g., a surgical stage detection algorithm) and/or trigger conditions, and the system may then automatically determine whether all required filters (and no impermissible filters) are installed for operation in the desired imaging mode. Optionally, the system may automatically select an imaging mode from a set of available imaging modes, wherein the imaging mode may be selected by identifying a mode for which operational requirements are met by the filters that were determined to be installed.

In some aspects, an imaging mode may comprise a predetermined set of one or more settings in which the system may operate for illumination, image capture, and/or image processing.

In some aspects, an imaging mode may include an image capture mode that designates one or one or more settings for operation of one or more image sensors of the system during image capture. For example, an image capture mode may designate exposure settings, aperture settings, ISO settings, shutter speed settings, and/or framerate settings.

In some aspects, an imaging mode may include an illumination mode that designates one or one or more settings for operation of one or more light sources of the system during illumination of a subject for imaging. For example, an illumination mode may designate intensity, wavelength, spot size, beam shape, polarization, and/or temporal profile of illumination light to illuminate the subject to be imaged.

In some aspects, an imaging mode may include an image processing mode that designates one or one or more settings for one or more image processing operations performed by the system on any of the images captured of the subject. For example, an illumination mode may designate a manner in which an image is processed with one or more preprocessing algorithms, compression algorithms, image enhancement algorithms, object identification algorithms, and/or classification algorithms.

At block 216, the system may set the imaging device to the selected or approved imaging mode. If the imaging mode includes an illumination mode, the system may configure the light source(s) in accordance with the illumination mode. If the imaging mode includes an image capture mode, the system may configure the image sensor(s) in accordance with the image capture mode. If the imaging mode includes an image processing mode, the system may configure one or more processors of the system in accordance with the image processing mode.

In some aspects, the system may display an indication of a selected or approved imaging mode, for example before automatically setting the system to the selected or approved mode, or to allow a user to confirm selection of the mode before setting the system to the selected mode in response to the user's confirmation.

At block 218, the system may perform illumination, capture and/or processing of an image of subject tissue using the selected/approved and set imaging mode. It should be noted that illumination may be performed using one or more of the same light sources that were used for emission of light during filter testing, capture of images may be performed using one or more of the same image sensors that were used for detection of reflected light during filter testing, and processing of captured images of the subject may be performed using one or more of the same processors that were used for filter identification and mode selection in accordance with filter testing. In this manner, rather than requiring manual identification or testing of filters, and rather than requiring testing of filters using a separate dedicated inspection device, the filter testing functionality may be provided using the same hardware that is leveraged for imaging of the subject. Thus, compactness, efficiency, affordability, and case of use of the system may be improved.

In some embodiments, in addition to or alternatively to detecting and identifying installed filters using reflected light from emission pulses having different optical properties from one another (e.g., where the reflection is reflected from a white balance card), the system may detect and identify installed filters based on light reflected from a multicolor test target. For example, the system may illuminate a multicolor test target with a single color or wavelength range of light (e.g., white light) or may allow the multicolor test target to be illuminated under ambient light conditions, and may then capture an image of the multicolor test target. By assessing colors of the captured image at a plurality of locations in the image corresponding to known colors, the system may determine whether transmission of any wavelengths to the image sensor are blocked, and may determine on that basis the identity of any one or more optical filters that are present in the optical collection path of the system.

Example #1

In a prophetic example of a system and method in accordance with the disclosure herein, a system with a light source providing the following wavelengths is provided:

NIR Laser wavelength: 806/808 nm
Laser wavelength: 780 nm
NIR laser wavelength: 780 nm
Blue Light diode center: 410 nm A filter testing process includes the following steps:

1.) A user instructs the system to execute a white balance process, which triggers a filter-detection process.
2.) Light source of the system and camera of the system communicate with one another to execute the following illumination and detection steps:
   a. NIR laser output initiates
   b. Camera detects reflected NIR light, if it is not blocked by a filter from transmission to the camera
   c. NIR laser output ceases
   d. UV diode output initiates
   e. Camera detects reflected UV light, if it is not blocked by a filter from transmission to the camera
   f. UV diode output ceases
3.) The system analyzes reflected light from the illumination in the previous step to determine which filter(s) are present in the optical collection path.
4.) The light source outputs white light.
5.) The camera executes white balance.

The analysis at Step 3 may include the following for NIR filter detection. If a red sensor of the camera is flooded with signal at step 2(b) (e.g., signal intensity is above a threshold intensity level), the system may determine that a NIR-blocking filter is not present. If the red sensor does not receive significant change in signal intensity at step 2(b) (e.g., signal intensity is below a threshold intensity level), the system may determine that a NIR-blocking filter is present.

The analysis at Step 3 may include the following for blue light filter detection. If a blue sensor of the camera is flooded with signal at step 2(e) (e.g., signal intensity is above a threshold intensity level), the system may determine that a blue-light-blocking filter is not present. If the blue sensor does not receive significant change in signal intensity at step 2(e) (e.g., signal intensity is below a threshold intensity level), the system may determine that a blue-light-blocking filter is present.

Example #2

In a prophetic example of a system and method in accordance with the disclosure herein, the following table shows filter testing outcomes when various filters are present or absent (as indicated in the leftmost column) under a variety of illumination conditions (as shown across the top row). The cells of the table indicate, for each combination of filter condition and illumination condition, the following:

- a characterization of the overall color of the image that is detected by a camera of the system under the specified conditions (as indicated by "*") (note that "'Normal' image" indicates an image color characteristic of an image captured without illumination, e.g., with a light source deactivated under ambient/room light);
- what action may be taken in response to identification of the filter (as indicated by "**"); and
- what potential imaging impact the identified filter may have (as indicated by "****").

TABLE 1

| | NIR 808 Laser | NIR 780 Laser | UV Diode, 410 nm Diode Center |
|---|---|---|---|
| No filter | *Pink image<br>**CCU disables NIR modes<br>***None | *Pink image<br>**CCU disables NIR modes<br>***None | *Blue Image<br>**CCU disables Blue Light Cystoscopy mode<br>***Cannot visualize 5ala |
| 680-825 nm rejection | *'Normal' image<br>**CCU enables NIR modes<br>***Cannot visualize OTL38 fluorescence | *'Normal' image<br>**CCU enables NIR modes<br>***Usable image, but possibly less ICG fluorescence signal than "normal" | *Blue Image<br>**CCU disables Blue Light Cystoscopy mode<br>***Cannot visualize 5ala |
| 685-800 nm rejection | *Pink image<br>**CCU disables NIR modes<br>***Cannot visualize ICG/OTL38 | *'Normal' image<br>**CCU enables NIR modes<br>***None, though not intended for ICG visualization | *Blue Image<br>**CCU disables Blue Light Cystoscopy mode<br>***Cannot visualize 5ala |
| 700-825 nm rejection | *'Normal' image<br>**CCU enables NIR modes<br>***Cannot visualize OTL38 fluorescence | *'Normal' image<br>**CCU enables NIR modes<br>***Usable image, but possibly less ICG fluorescence signal than "normal." | *Blue Image<br>**CCU disables Blue Light Cystoscopy mode<br>***Cannot visualize 5ala |
| 685 nm-800 nm rejection | *Pink image<br>**CCU disables NIR modes<br>***Cannot visualize ICG/OTL38 | *'Normal' image<br>**CCU enables NIR modes<br>***None | *Blue Image<br>**CCU disables Blue Light Cystoscopy mode<br>***Cannot visualize 5ala |
| Blue Light Filter, longpass at 455 nm | *Pink image<br>**CCU disables NIR modes<br>***Cannot visualize ICG/OTL38 | *Pink image<br>**CCU disables NIR modes<br>***Cannot visualize ICG/OTL38 | *'Normal' image<br>**CCU enables Blue Light Cystoscopy mode<br>***None |

For the combination of the 680-825 nm rejection filter with the NIR 780 Laser shown in Table 1, the system may be able to make a determination as to what filter(s) are present, but the mode that is enabled by the system may not be the mode that was intended for use.

For the combination of the 700-825 nm rejection filter with the NIR 780 Laser shown in Table 1, the system may be able to make a determination as to what filter(s) are present, but the mode that is enabled by the system may not be the mode that was intended for use.

For the combination of the 685-800 nm rejection filter with the NIR 780 Laser shown in Table 1, it may be unlikely that a system can make a determination in the field.

For the remaining combinations in Table 1 aside from the above three specifically-noted combinations, the system may be able to make a determination as to what filter(s) are present and may be able to efficiently and effectively enable/disable modes for use in the field based on that determination.

Example #3

Figure 3A:
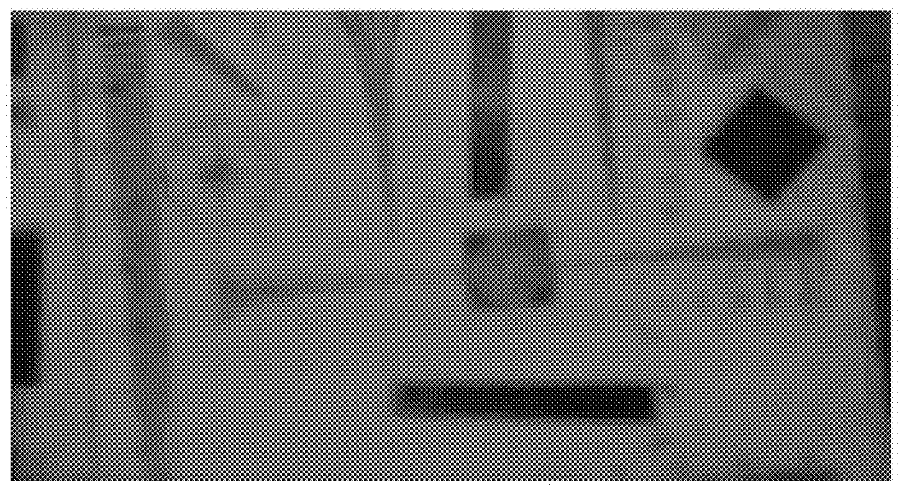
FIGS. 3A-3B show images captured without (3A) and with (3B) appropriate wavelength filters present during testing to determine whether a filter blocking NIR light is present in a collection path of the imaging system, according to some aspects.
Figure 3B:
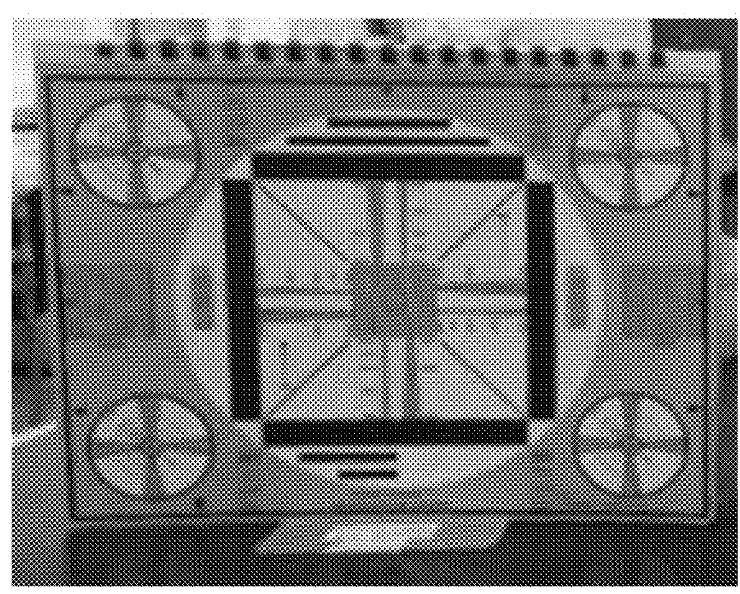

In one example, different images are captured under NIR illumination to automatically determine whether a wavelength filter for blocking reflected light from the NIR illumination is present in the imaging system. FIG. 3A shows an image captured under NIR laser diode illumination without an appropriate laser wavelength filter installed in the system, resulting in a "pink" image. FIG. 3B shows an image captured under NIR laser diode illumination with an appropriate laser wavelength filter installed in the system, resulting in a "normal" image.

Example #4

Figure 4A:
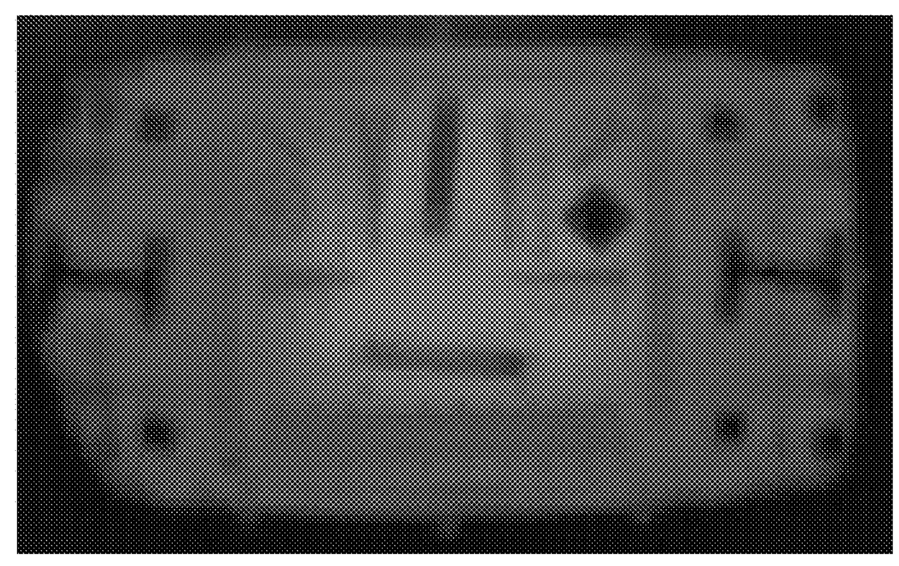
FIGS. 4A-4B show images captured without (4A) and with (4B) appropriate wavelength filters present during testing to determine whether a filter blocking blue light is present in a collection path of the imaging system, according to some aspects.
Figure 4B:
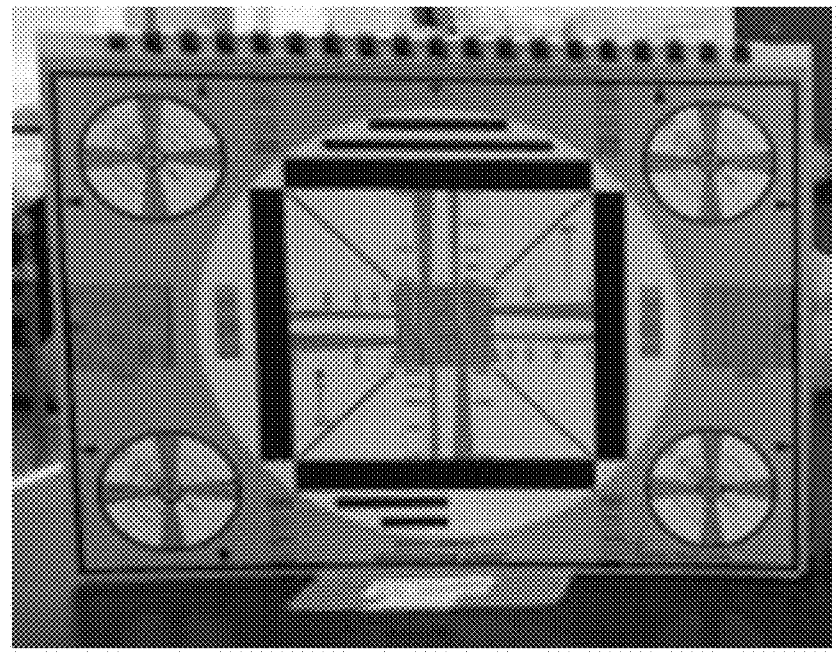

In one example, different images are captured under UV illumination to automatically determine whether a wavelength filter for blocking reflected light from the UV illumination is present in the imaging system. FIG. 4A shows an image captured under UV diode illumination without an appropriate blue light filter installed in the system, resulting in a "blue" image. FIG. 4B shows an image captured under UV diode illumination with an appropriate blue light filter installed in the system, resulting in a "normal" image.

Exemplary Computer

Figure 5:
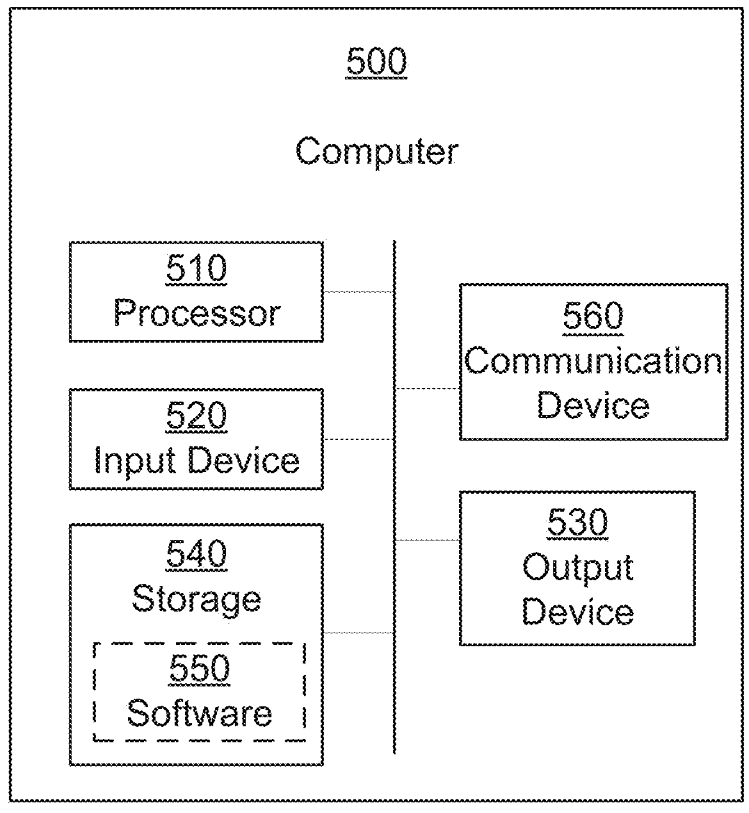
FIG. 5 shows a computing system, according to some aspects.

FIG. 5 illustrates an example of a computing system 500, in accordance with some examples of the disclosure. Computing system 500 can be a client or a server. As shown in FIG. 5, computing system 500 can be any suitable type of processor-based system, such as a personal computer, workstation, server, handheld computing device (portable electronic device) such as a phone or tablet, or dedicated device. The computing system 500 can include, for example, one or more of input device 520, output device 530, one or more processors 510, storage 540, and communication device 560. Input device 520 and output device 530 can either be connectable or integrated with computing system 500.

Input device 520 can be any suitable device that provides input, such as a touch screen, keyboard or keypad, mouse, gesture recognition component of a virtual/augmented reality system, or voice-recognition device. Output device 530 can be or include any suitable device that provides output, such as a display, touch screen, haptics device, virtual/augmented reality display, or speaker.

Storage 540 can be any suitable device that provides storage, such as an electrical, magnetic, or optical memory including a RAM, cache, hard drive, removable storage disk, or other non-transitory computer readable medium. Storage 540 can include one storage device or more than one storage device. As used herein, the terms storage, memory, and/or storage medium/media may refer to singular and/or plural devices which may store data and/or code/instructions individually, redundantly, and/or in cooperation with one another, for example in a local and/or cloud storage environment. Communication device 560 can include any suitable device capable of transmitting and receiving signals over a network, such as a network interface chip or device. The components of the computing system 500 can be connected in any suitable manner, such as via a physical bus or wirelessly.

Processor(s) 510 can be any suitable processor or combination of processors, including any of, or any combination of, a central processing unit (CPU), field programmable gate array (FPGA), and application-specific integrated circuit (ASIC). Software 550, which can be stored in storage 540 and executed by one or more processors 510, can include, for example, the programming that provides the functionality or portions of the functionality of the present disclosure (e.g., as described with respect to in the systems and methods as described above).

Software 550 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport computer readable medium can include, but is not limited to, an electronic, magnetic, optical, electromagnetic, or infrared wired or wireless propagation medium.

Computing system 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computing system 500 can implement any operating system suitable for operating on the network. Software 550 can be written in any suitable programming language, such as C, C++, Java, or Python. In various aspects, application software providing the functionality of the present disclosure can be deployed in different configurations, such as in a client/server arrangement or through a Web browser as a Web-based application or Web service, for example.

The foregoing description, for the purpose of explanation, has been described with reference to specific aspects and examples. However, the illustrative discussions above are not intended to be exhaustive or to limit the invention to the precise forms disclosed. Many modifications and variations are possible in view of the above teachings. The aspects and examples were chosen and described in order to best explain the principles of the techniques and their practical applications. Others skilled in the art are thereby enabled to best utilize the techniques and various aspects with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

For the purpose of clarity and a concise description, features are described herein as part of the same or separate examples; however, it will be appreciated that the scope of the disclosure includes examples having combinations of all or some of the features described.

The invention claimed is:

1. A system for identifying optical filters within a surgical imaging device, comprising:
- a set of one or more light sources;
- a set of one or more image sensors of the surgical imaging device;
- one or more processors; and
- memory storing instructions configured to be executed by the one or more processors to cause the system to:
  - emit, by the set of one or more light sources, a set of emission light pulses, wherein emitting the set of emission light pulses comprises emitting a predetermined time-series of the emission light pulses selected to differentiate between a predetermined set of optical filters, wherein one or more of the emission light pulses have different characteristic wavelengths from one another;
  - detect, by the set of one or more image sensors, reflection light of the one or more light pulses; and
  - determine, based at least in part on the detected reflection light, an identity of an optical filter of the surgical imaging device, wherein the optical filter is disposed in an optical collection path of the surgical imaging device.

2. The system of claim 1, wherein detecting the reflection light comprises detecting a set of collection light pulses, wherein one or more of the collection light pulses have different characteristic wavelengths from one another.

3. The system of claim 1, wherein determining the identity of the optical filter based at least in part on the detected reflection light comprises determining whether the detected reflection light exceeds a threshold intensity in a predetermined wavelength range.

4. The system of claim 1, wherein determining the identity of the optical filter based at least in part on the detected reflection light comprises determining whether a first image sensor of the set of one or more image sensors is activated above a threshold intensity.

5. The system of claim 1, wherein determining the identity of the optical filter based at least in part on the detected reflection light comprises determining that the reflection light comprises a number of collection light pulses that is fewer than a number of emission light pulses emitted in the set of emission light pulses.

6. The system of claim 1, wherein:
- detecting the reflection light comprises detecting multiple collection light pulses; and
- determining the identity of the optical filter based at least in part on the detected reflection light comprises determining the identity of the optical filter based at least in part on relative intensities of the multiple collection light pulses.

7. The system of claim 1, wherein determining the identity of the optical filter comprises looking up the identity of the filter based on stored data indicating an association between a characteristic of the detected reflection light and the identity of the optical filter.

8. The system of claim 1, wherein determining the identity of the optical filter comprises:
- determining, based at least in part on the detected reflection light, one or more optical characteristics of the optical filter; and
- determining, based at least in part on the determined one or more optical characteristics, the identity of the optical filter.

9. The system of claim 8, wherein the instructions are configured to be executed by the one or more processors to cause the system to, after determining the identity of the optical filter, determine one or more additional optical characteristics of the optical filter, different from the one or more optical characteristics, based on the determined identity of the optical filter.

10. The system of claim 1, wherein the instructions are configured to be executed by the one or more processors to cause the system to, after determining the identity of the optical filter, capture, by the set of one or more image sensors, an image of a subject.

11. The system of claim 10, wherein:
- the instructions are configured to be executed by the one or more processors to cause the system to:
  - select an image capture mode based at least in part on the determined identity of the optical filter; and
  - set the set of one or more image sensors to the selected image capture mode; and
- capturing the image of the subject comprises capturing the image in accordance with the image capture mode.

12. The system of claim 10, wherein:
- the instructions are configured to be executed by the one or more processors to cause the system to approve a selected image capture mode for the set of one or more image sensors based at least in part on the determined identity of the optical filter; and
- capturing the image of the subject comprises capturing the image in accordance with the selected image capture mode.

13. The system of claim 1, wherein the instructions are configured to be executed by the one or more processors to cause the system to, after determining the identity of the optical filter, illuminate, by the one or more light sources, a subject to be imaged by the system.

14. The system of claim 13, wherein:
- the instructions are configured to be executed by the one or more processors to cause the system to:
  - select an illumination mode based at least in part on the determined identity of the optical filter; and
  - set the set of one or more light sources to the selected illumination mode; and
- illuminating the subject comprises illuminating the subject in accordance with the illumination mode.

15. The system of claim 13, wherein:
- the instructions are configured to be executed by the one or more processors to cause the system to approve a selected illumination mode for the set of one or more light sources based at least in part on the determined identity of the optical filter; and illuminating the subject comprises illuminating the subject in accordance with the illumination mode.

16. The system of claim 1, wherein the instructions are configured to be executed by the one or more processors to cause the system to, after determining the identity of the optical filter, perform an image processing operation on an image captured through the optical filter.

17. The system of claim 16, wherein:

the instructions are configured to be executed by the one or more processors to cause the system to:

select an image processing mode based at least in part on the determined identity of the optical filter; and set the set of system to the selected image processing mode; and performing the image processing operation comprises performing the image processing operation in accordance with the image processing mode.

18. The system of claim 16, wherein:

the instructions are configured to be executed by the one or more processors to cause the system to approve a selected image processing mode for the system based at least in part on the determined identity of the optical filter; and performing the image processing operation comprises performing the image processing operation in accordance with the image processing mode.

19. The system of claim 1, wherein the instructions are configured to be executed by the one or more processors to cause the system to:

select a mode for the system based at least in part on the determined identity of the optical filter; and set the set of system to the selected mode.

20. The system of claim 1, wherein the instructions are configured to be executed by the one or more processors to cause the system to:

approve a selected mode for the system based at least in part on the determined identity of the optical filter.

21. The system of claim 1, wherein the optical filter is disposed in a coupler of the system.

22. The system of claim 1, wherein the optical filter is disposed between the surgical imaging device and a coupler of the system.

23. The system of claim 1, wherein the surgical imaging device comprises an endoscope and the optical filter is disposed in the endoscope.

24. A non-transitory computer-readable storage medium storing instructions for identifying optical filters within a surgical imaging device, the instructions configured to be executed by one or more processors of system comprising a set of one or more light sources and a set of one or more image sensors of the surgical imaging device, to cause the system to:

emit, by the set of one or more light sources, a set of emission light pulses, wherein emitting the set of emission light pulses comprises emitting a predetermined time-series of the emission light pulses selected to differentiate between a predetermined set of optical filters, wherein one or more of the emission light pulses have different characteristic wavelengths from one another;

detect, by the set of one or more image sensors, reflection light of the one or more light pulses; and determine, based at least in part on the detected reflection light, an identity of an optical filter of the surgical imaging device, wherein the optical filter is disposed in an optical collection path of the surgical imaging device.

25. A method for identifying optical filters within a surgical imaging device, the method performed by a system comprising a set of one or more light sources, a set of one or more image sensors of the surgical imaging device, and one or more processors, the method comprising:

emitting, by the set of one or more light sources, a set of emission light pulses, wherein emitting the set of emission light pulses comprises emitting a predetermined time-series of the emission light pulses selected to differentiate between a predetermined set of optical filters, wherein one or more of the emission light pulses have different characteristic wavelengths from one another;

detecting, by the set of one or more image sensors, reflection light of the one or more light pulses; and determining, based at least in part on the detected reflection light, an identity of an optical filter of the surgical imaging device, wherein the optical filter is disposed in an optical collection path of the surgical imaging device.

* * * * *